(12) United States Patent
Keenan et al.

(10) Patent No.: US 8,552,019 B2
(45) Date of Patent: Oct. 8, 2013

(54) INHIBITORS OF PHOSPHOINOSITIDE DEPENDENT KINASE 1 (PDK1)

(75) Inventors: Kevin A. Keenan, Watertown, MA (US); Alan B. Northrup, Reading, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 115 days.

(21) Appl. No.: 13/131,322

(22) PCT Filed: Nov. 24, 2009

(86) PCT No.: PCT/US2009/065606
§ 371 (c)(1),
(2), (4) Date: May 26, 2011

(87) PCT Pub. No.: WO2010/065384
PCT Pub. Date: Jun. 10, 2010

(65) Prior Publication Data
US 2011/0230500 A1 Sep. 22, 2011

Related U.S. Application Data

(60) Provisional application No. 61/120,090, filed on Dec. 5, 2008.

(51) Int. Cl.
*A61K 31/505* (2006.01)
(52) U.S. Cl.
USPC .......... 514/269; 544/269; 548/306.4

(58) Field of Classification Search
USPC .......... 514/269; 544/333; 548/306.4
See application file for complete search history.

(56) References Cited

U.S. PATENT DOCUMENTS

2004/0019067 A1  1/2004  Armistead et al.

OTHER PUBLICATIONS

Biondi, Ricardo, M. et al., "High Resolution crystal structure of the human PDK1 catalytic domain defines the regulatory phosphopeptide docketing site"; The EMBO Journal, vol. 21, No. 16; pp: 4219-4228; 2002.

*Primary Examiner* — Douglas M Willis
(74) *Attorney, Agent, or Firm* — Yong Zhao; David A. Muthard; Matthew A. Leff

(57) ABSTRACT

The instant invention provides for compounds of formula A that inhibit PDK1 activity:

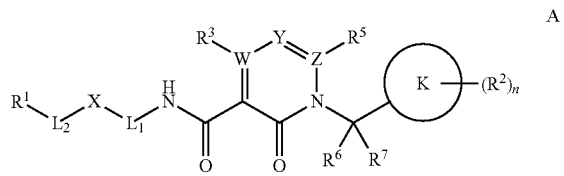

The invention also provides for compositions comprising such inhibitory compounds and methods of inhibiting PDK1 activity by administering the compound to a patient in need of treatment of cancer.

5 Claims, No Drawings

INHIBITORS OF PHOSPHOINOSITIDE DEPENDENT KINASE 1 (PDK1)

REFERENCE TO SEQUENCE LISTING SUBMITTED ELECTRONICALLY

The sequence listing of the present application is being submitted electronically via EFS-Web as an ASCII formatted sequence listing with a file name "MRLONC00006USPCT-SEQTXT-24MAY2011.txt", creation date of May 24, 2011 and a size of 748 bytes. This sequence listing submitted via EFS-Web is part of the specification and is herein incorporated by reference in its entirety.

BACKGROUND OF THE INVENTION

3-Phosphoinositide-dependent protein kinase-1 (PDK1) is a 556-amino acid containing enzyme comprised of a C-terminal Pleckstrin homology (PH) domain (residues 459-550) and an N-terminal kinase domain (residues 70-359). The PH domain of PDK1 binds phosphatidylinositols (e.g., phosphatidylinositol 4,5-bisphosphate and phosphatidylinositol 3,4,5-triphosphate) produced by phosphatidylinositol kinases, such as phosphatidylinositol 3-kinase (PI3K) and whose levels are, in part, controlled by phosphatases such as PTEN (phosphatase and tensin homologue). PDK1 plays a central role in the PI3K/Akt pathway and has been called a "master regulator" kinase due to its role as a critical upstream activating kinase that phosphorylates the so-called T-loop phosphorylation site for multiple kinases in the AGC family of kinases including but not limited to all three isoforms of PKB (PKBα, PKBβ, PKBγ, also known as Akt1, Akt2, and Akt3, respectively), RSK (three isoforms RSK1, RSK2, RSK3, also known as p90RSK), p70S6K (two isoforms, S6K1 and S6K2), SGK1 and PKC.

Signals from several peptide growth factors including insulin, insulin-like growth factor-1 and platelet-derived growth factor are transduced by PKB. Like PDK1, PKB contains a PH domain that binds phosphatidyl 3,4,5-triphosphate. PKB is translocated to the plasma membrane and phosphorylated by PDK1 at residue T-308/309 (the two phosphosites correspond to different isoforms) in response to the second messenger phosphatidyl 3,4,5-triphosphate produced by PI3K. Activation of PKB in tumor cells results in increased cellular survival via anti-apoptotic signals and also proliferation. PKBβ amplification has been observed in a proportion of several tumor types including ovarian, breast and pancreatic cancers. Similarly, PKBα amplification has been observed in a percentage of gastric adenocarcinoma samples. Recently, an activated mutant form of PKBα (E17K) was detected in a number of breast (8%), colorectal (6%), and ovarian (2%) cancers. PDK1 kinase inhibitors are useful as treatments for diseases linked to PKB signaling (such as cancer, Cowden syndrome, Lhermitte-Dudos disease and Bannayan-Zonana syndrome) by preventing activation of PKB signaling by PDK1.

Similarly, PDK1 kinase inhibitors are useful for treating cancer or other proliferative disorders by blocking the activation of p70S6K by PDK1. There are several substrates of p70S6K, such as ribosomal S6 protein, eIF4B, PDCD4 etc., that are involved in translation inhibition complex formation or ribosomal protein synthesis. Inhibition of protein synthesis via inhibition of phosphorylation of ribosomal S6 protein is believed to inhibit the proliferation of tumor cells by mTOR inhibitors (e.g., rapamycin). p70S6K gene amplification has been observed in breast tumor specimens. Simultaneous amplification of p70S6K and HER-2 correlates with poor survival in cancer patients. Hyperactivation of p70S6K (as measured by phosphorylation of T389) has been observed by immunohistochemical analysis of breast, head and neck squamous cell carcinoma (HNSCC), glioblastoma, lung and liver primary tumor specimens.

Likewise, PDK1 kinase inhibitors are useful for the treatment of cancer by blocking the activation of RSK1 (also known as p90RSK) by PDK1. RSK1 transduces anti-apoptotic and proliferative signals be mediating phosphorylation directly or indirectly of BAD, LKB1, TSC2, NFkB, mTOR. Ras/MAPK pathway is activated in >50% in primary tumors. RSK1 activity is correlated with MAPK activity. RSK1 is overexpressed in primary breast and prostate cancer samples.

PDK1 signaling regulates multiple critical steps in angiogenesis. Inhibitors of the activity of PDK1 are thus useful in the treatment of cancer, in particular cancers associated with deregulated activity of the PTEN/PI3K pathway including, but not limited to PTEN loss of function mutations, PI3K gain of function mutations and receptor tyrosine kinase gain of function mutations.

PDK1 signaling has also been implicated in tumorigenesis and a PDK1 inhibitor is useful for tumor prevention or prevention of tumor recurrence. Mice with a PTEN heterozygous (PTEN$^{+/-}$) genotype are well-known to spontaneously develop tumors. Alessi and co-workers found that PDK1 hypomorphic PTEN$^{+/-}$ mice expressing <30% of normal PDK1 protein levels showed a significant delay in tumor formation as compared to littermate controls expressing normal levels of PDK1 protein (Current Biology, 2005, 15, 1839-1846).

SGK1 (serum and glucocorticoid-regulated kinase-1) activity is critical for insulin-mediated Na+ retention and hypertensive effects. Inhibition of SGK1 activity by a PDK1 kinase inhibitor is useful in treating hypertension and/or hypoinsulinemia.

It is an object of the instant invention to provide novel compounds that are inhibitors of PDK1.

It is also an object of the present invention to provide pharmaceutical compositions that comprise the novel compounds that are inhibitors of PDK1.

It is also an object of the present invention to provide a method for treating cancer that comprises administering such inhibitors of PDK1 activity.

It is also an object of the present invention to provide a method for treating tumor recurrence that comprises administering such inhibitors of PDK1 activity.

It is also an object of the present invention to provide a method for treating hypertension that comprises administering such inhibitors of PDK1 activity.

It is also an object of the present invention to provide a method for treating diabetes mellitus that comprises administering such inhibitors of PDK1 activity.

SUMMARY OF THE INVENTIONS

The instant invention provides for compounds that inhibit PDK1 activity. The invention also provides for compositions comprising such inhibitory compounds and methods of inhibiting PDK1 activity by administering the compound to a patient in need of treatment of cancer.

DETAILED DESCRIPTION OF THE INVENTION

The compounds of the instant invention are useful in the inhibition of the activity of PDK1. In a first embodiment of this invention, the inhibitors of PDK1 activity are illustrated by the Formula A:

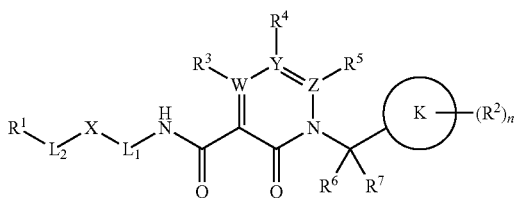

A wherein:

n is 0, 1, 2, 3, 4 or 5;

W is independently C or N, Y is independently C or N, Z is independently C or N, with the proviso that at least one of W, Y and Z is N;

X is O, $CH_2$ or NH;

Ring K is aryl or heteroaryl;

$L_1$ is $C_0$-$C_6$ alkyl, $C_2$-$C_6$ alkenyl or heteroaryl, wherein said alkyl is optionally substituted with $C_1$-$C_6$ alkyl or phenyl, wherein said phenyl is optionally substituted with $C_1$-$C_6$ alkyl, $C_1$-$C_6$ alkyl-OH, O($C_1$-$C_6$)alkyl, halo and OH;

$L_2$ is $C_0$-$C_6$ alkyl, $C_2$-$C_6$ alkenyl or heteroaryl, wherein said alkyl is optionally substituted with $C_1$-$C_6$ alkyl or phenyl;

$R^1$ is heterocyclyl which is optionally substituted with $C_1$-$C_6$ alkyl, $C_1$-$C_6$ alkyl-OH, O($C_1$-$C_6$)alkyl, NH(C=O)$C_1$-$C_6$ alkyl, $C_2$-$C_6$ alkenyl, $CO_2H$, halo, OH, oxo and $NR^8R^9$;

$R^2$ is independently selected from: H, $C_1$-$C_6$ alkyl, $C_1$-$C_6$ alkyl-OH, O($C_1$-$C_6$)alkyl, $C_2$-$C_6$ alkenyl, $CO_2H$, halo, OH and $NR^8R^9$;

$R^3$ is selected from: H, $C_1$-$C_6$ alkyl, $C_1$-$C_6$ alkyl-OH, O($C_1$-$C_6$)alkyl, $C_2$-$C_6$ alkenyl, $CO_2H$, halo, OH and $NR^8R^9$;

$R^4$ is selected from: H, $C_1$-$C_6$ alkyl, $C_1$-$C_6$ alkyl-OH, O($C_1$-$C_6$)alkyl, $C_2$-$C_6$ alkenyl, $CO_2H$, halo, OH and $NR^8R^9$;

$R^5$ is selected from: H, $C_1$-$C_6$ alkyl, $C_1$-$C_6$ alkyl-OH, O($C_1$-$C_6$)alkyl, $C_2$-$C_6$ alkenyl, $CO_2H$, halo, OH and $NR^8R^9$;

$R^6$ and $R^7$ are independently selected from: H and $C_1$-$C_6$ alkyl; and $R^8$ and $R^9$ are independently selected from: H and $C_1$-$C_6$ alkyl;

or a pharmaceutically acceptable salt or a stereoisomer thereof.

In a second embodiment of this invention, the inhibitors of PDK1 activity are illustrated by the Formula B:

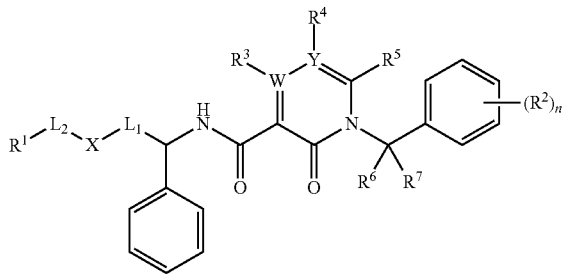

B wherein:

n is 1, 2 or 3;

W is independently C or N and Y is independently C or N, with the proviso that at least one of W or Y is N;

X is O, $CH_2$ or NH;

$L_1$ is $C_0$-$C_5$ alkyl or $C_2$-$C_5$ alkenyl;

$L_2$ is $C_0$-$C_6$ alkyl, $C_2$-$C_6$ alkenyl or heteroaryl, wherein said alkyl is optionally substituted with $C_1$-$C_6$ alkyl or phenyl;

$R^1$ is heterocyclyl which is optionally substituted with $C_1$-$C_6$ alkyl, $C_1$-$C_6$ alkyl-OH, O($C_1$-$C_6$)alkyl, NH(C=O)$C_1$-$C_6$ alkyl, $C_2$-$C_6$ alkenyl, $CO_2H$, halo, OH, oxo and $NR^8R^9$;

$R^2$ is halo;

$R^3$ is selected from: H, $C_1$-$C_6$ alkyl, $C_1$-$C_6$ alkyl-OH, O($C_1$-$C_6$)alkyl, $C_2$-$C_6$ alkenyl, $CO_2H$, halo, OH and $NR^8R^9$;

$R^4$ is selected from: H, $C_1$-$C_6$ alkyl, $C_1$-$C_6$ alkyl-OH, O($C_1$-$C_6$)alkyl, $C_2$-$C_6$ alkenyl, $CO_2H$, halo, OH and $NR^8R^9$;

$R^5$ is selected from: H, $C_1$-$C_6$ alkyl, $C_1$-$C_6$ alkyl-OH, O($C_1$-$C_6$)alkyl, $C_2$-$C_6$ alkenyl, $CO_2H$, halo, OH and $NR^8R^9$;

$R^6$ and $R^7$ are independently selected from: H and $C_1$-$C_6$ alkyl; and $R^8$ and $R^9$ are independently selected from: H and $C_1$-$C_6$ alkyl;

or a pharmaceutically acceptable salt or a stereoisomer thereof.

In a third embodiment of this invention, the inhibitors of PKD1 activity are illustrated by the Formula C:

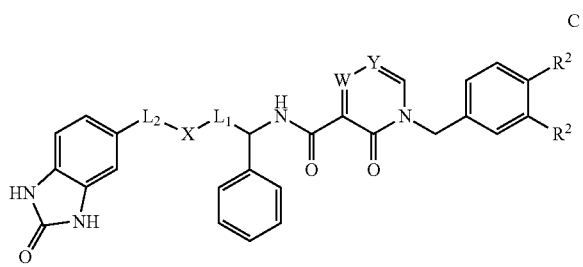

C wherein:

W is independently CH or N and Y is independently CH or N, with the proviso that at least one of W or Y is N;

X is O or $NH_2$;

$L_1$ is $C_0$-$C_3$ alkyl;

$L_2$ is $C_0$-$C_3$ alkyl; and $R^2$ is halo;

or a pharmaceutically acceptable salt or a stereoisomer thereof.

Specific compounds of the instant invention include:

1-(3,4-difluorobenzyl)-6-oxo-N-{(1R)-2-[(2-oxo-2,3-dihydro-1H-benzimidazol-5-yl)oxy]-1-phenylethyl}-1,6-dihydropyrimidine-5-carboxamide; and 4-(3,4-difluorobenzyl)-3-oxo-N-{(1R)-2-[(2-oxo-2,3-dihydro-1H-benzimidazol-5-yl)oxy]-1-phenylethyl}-3,4-dihydropyrazine-2-carboxamide;

or a pharmaceutically acceptable salt or a stereoisomer thereof.

The compounds of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted.

When any variable (e.g. $R^2$) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is bicyclic, it is intended that the bond be attached to any of the suitable atoms on either ring of the bicyclic moiety.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

It is understood that one or more Si atoms can be incorporated into the compounds of the instant invention by one of ordinary skill in the art to provide compounds that are chemically stable and that can be readily synthesized by techniques known in the art from readily available starting materials.

As used herein, "alkyl" is intended to include both branched and straight-chain saturated aliphatic hydrocarbon groups having the specified number of carbon atoms. For example, $C_1$-$C_6$, as in "$C_1$-$C_6$ alkyl" is defined to include groups having 1, 2, 3, 4, 5 or 6 carbons in a linear or branched arrangement. For example, "$C_1$-$C_6$ alkyl" specifically includes methyl, ethyl, n-propyl, i-propyl, n-butyl, t-butyl, i-butyl, pentyl, hexyl, and so on.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

As appreciated by those of skill in the art, "halo" or "halogen" as used herein is intended to include chloro (Cl), fluoro (F), bromo (Br) and iodo (I).

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic, tricyclic, tetracyclic groups. "Heterocyclyl" therefore includes the above mentioned heteroaryls, as well as dihydro and tetrahydro analogs thereof. Further examples of "heterocyclyl" include: benzoimidazolyl, benzofuranyl, benzofurazanyl, benzopyrazolyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisochromenyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydroisoquinolinyl, tetrahydroquinolinyl and tetrahydrothienyl, and N-oxides thereof. Attachment of a heterocyclyl substituent can occur via a carbon atom or via a heteroatom.

In an embodiment of Formula A, Ring K is phenyl.

In another embodiment of Formula A, Z is CH.

In another embodiment of Formula A, X is O.

In an embodiment of Formula A, X is $NH_2$.

In another embodiment of Formula A, X is $CH_2$, $L_1$ is $C_0$-$C_3$ alkyl, wherein said alkyl is substituted with phenyl.

In another embodiment of Formula A, X is $NH_2$, $L_1$ is $C_0$-$C_3$ alkyl, wherein said alkyl is substituted with phenyl.

In another embodiment of Formula A, $L_2$ is $C_0$-$C_3$ alkyl.

In another embodiment of Formula A, $L_2$ is absent.

In another embodiment of Formula A, $R^1$ is selected from the following:

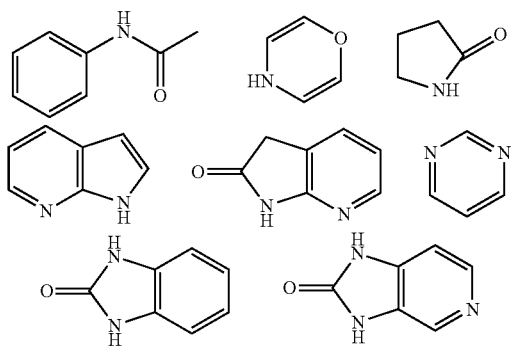

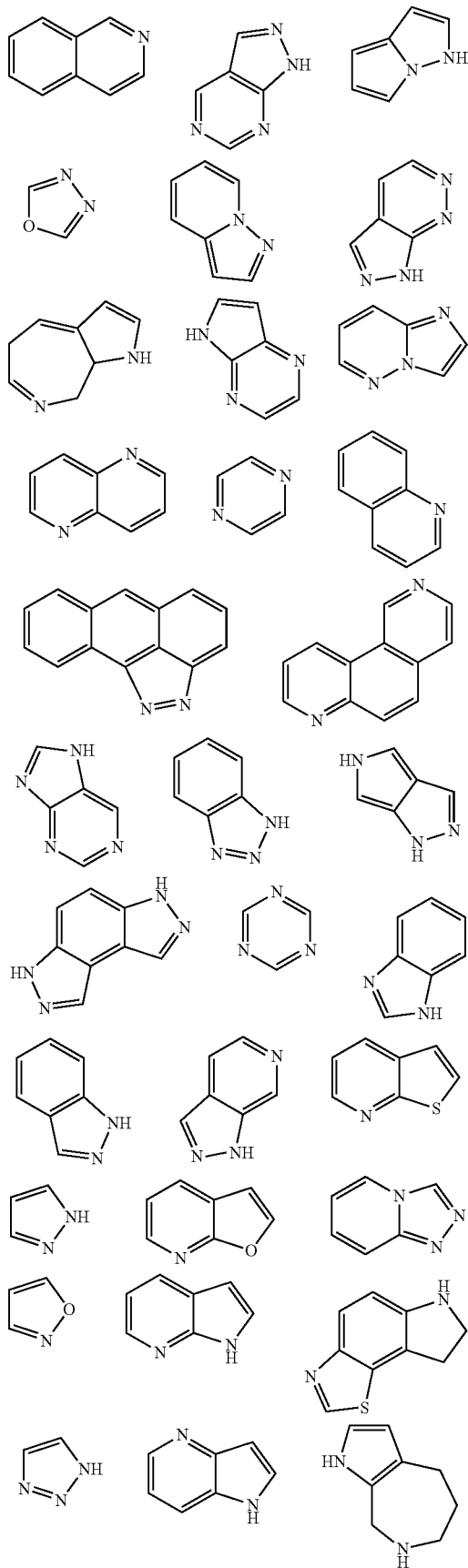
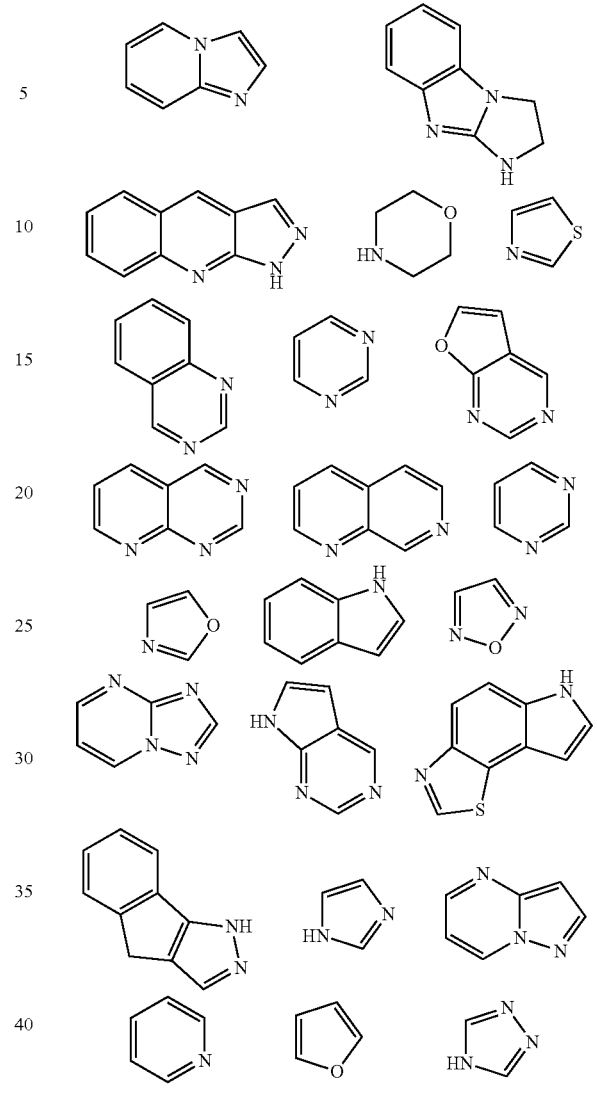

which are optionally substituted with $C_1$-$C_6$ alkyl, $C_1$-$C_6$ alkyl-OH, O($C_1$-$C_6$)alkyl, $C_2$-$C_6$ alkenyl, $CO_2H$, halo, OH and $NR^8R^9$.

In another embodiment of Formula A, $R^2$ is halo.

In another embodiment of Formula A, $R^2$ is F.

In another embodiment of Formula A, $R^3$ is selected from: H and halo.

In another embodiment of Formula A, $R^4$ is selected from: H and halo.

In another embodiment of Formula A, $R^5$ is selected from: H and halo.

In another embodiment of Formula A, $R^6$ and $R^7$ are H.

In an embodiment of Formula B, X is O.

In an embodiment of Formula B, X is $CH_2$.

In an embodiment of Formula B, X is $NH_2$.

In another embodiment of Formula B, $L_1$ is $C_0$-$C_3$ alkyl.

In another embodiment of Formula B, $L_2$ is $C_0$-$C_3$ alkyl.

In another embodiment of Formula B, $R^1$ is selected from the following:

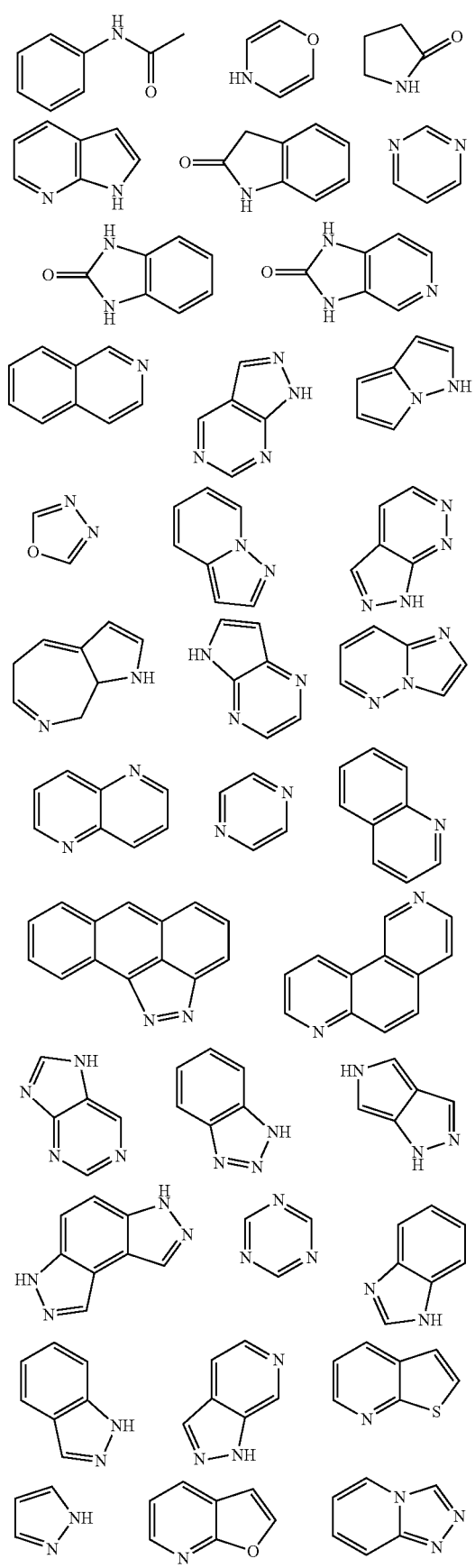
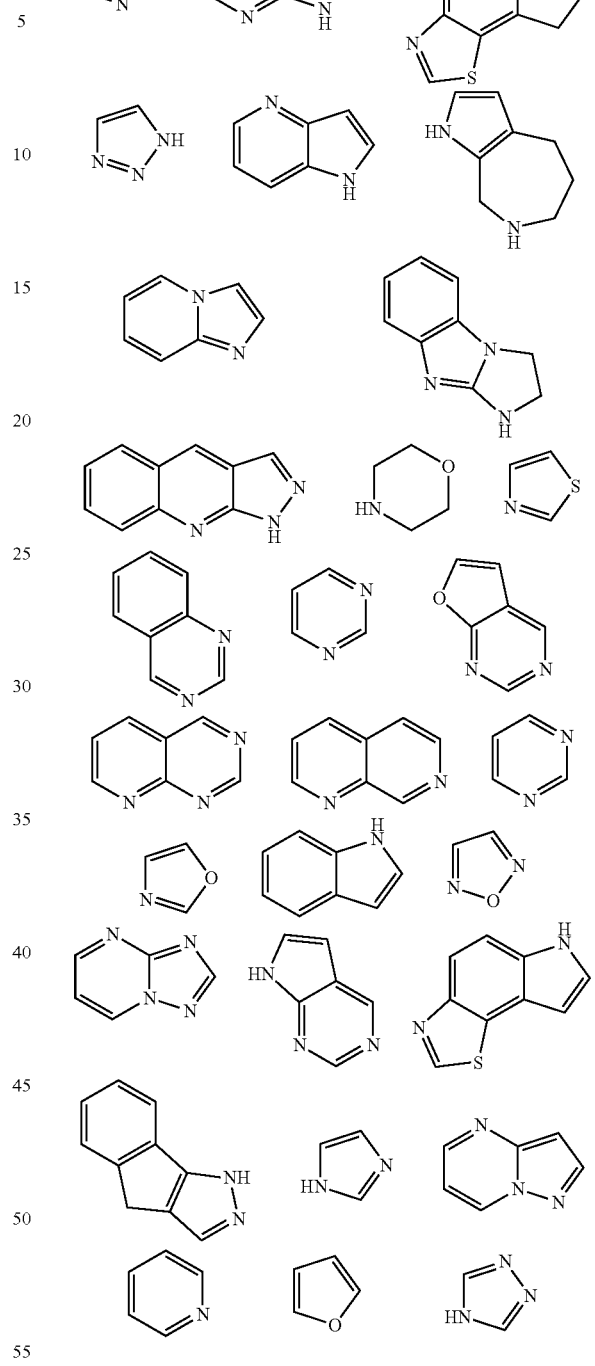

which are optionally substituted with $C_1$-$C_6$ alkyl, $C_1$-$C_6$ alkyl-OH, O($C_1$-$C_6$)alkyl, $C_2$-$C_6$ alkenyl, $CO_2H$, halo, OH and $NR^8R^9$.

In another embodiment of Formula B, $R^2$ is halo.
In another embodiment of Formula B, $R^2$ is F.
In another embodiment of Formula B, $R^3$ is selected from: H and halo.
In another embodiment of Formula B, $R^4$ is selected from: H and halo.
In another embodiment of Formula B, $R^5$ is selected from: H and halo.

In another embodiment of Formula B, $R^6$ and $R^7$ are H.
In another embodiment of Formula C, X is O.
In another embodiment of Formula C, X is HN.
In another embodiment of Formula C, $L_1$ is $CH_2$.
In another embodiment of Formula C, $L_2$ is absent.
In an embodiment of Formula C, $R^2$ is F.

Included in the instant invention is the free form of compounds of Formula A, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of Formula A. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977: 66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

Utility

3-Phosphoinositide-dependent protein kinase-1 (PDK1) is a 556-amino acid containing enzyme comprised of a C-terminal Pleckstrin homology (PH) domain (residues 459-550) and an N-terminal kinase domain (residues 70-359). The PH domain of PDK1 binds phosphatidylinositols (e.g., phosphatidylinositol 4,5-bisphosphate and phosphatidylinositol 3,4,5-triphosphate) produced by phosphatidylinositol kinases, such as phosphatidylinositol 3-kinase (PI3K) and whose levels are, in part, controlled by phosphatases such as PTEN (phosphatase and tensin homologue). PDK1 plays a central role in the PI3K/Akt pathway and has been called a "master regulator" kinase due to its role as a critical upstream activating kinase that phosphorylates the so-called T-loop phosphorylation site for multiple kinases in the AGC family of kinases including but not limited to all three isoforms of PKB (PKBα, PKBβ, PKBγ, also known as Akt1, Akt2, and Akt3, respectively), RSK (three isoforms RSK1, RSK2, RSK3, also known as p90RSK), p70S6K (two isoforms, S6K1 and S6K2), SGK1 and PKC.

Signals from several peptide growth factors including insulin, insulin-like growth factor-1 and platelet-derived growth factor are transduced by PKB. Like PDK1, PKB contains a PH domain that binds phosphatidyl 3,4,5-triphosphate. PKB is translocated to the plasma membrane and phosphorylated by PDK1 at residue T-308/309 (the two phosphosites correspond to different isoforms) in response to the second messenger phosphatidyl 3,4,5-triphosphate produced by PI3K. Activation of PKB in tumor cells results in increased cellular survival via anti-apoptotic signals and also proliferation. PKBβ amplification has been observed in a proportion of several tumor types including ovarian, breast and pancreatic cancers. Similarly, PKBα amplification has been observed in a percentage of gastric adenocarcinoma samples. Recently, an activated mutant form of PKBα (E17K) was detected in a number of breast (8%), colorectal (6%), and ovarian (2%) cancers. PDK1 kinase inhibitors are useful as treatments for diseases linked to PKB signaling (such as cancer, Cowden syndrome, Lhermitte-Dodos disease and Bannayan-Zonana syndrome) by preventing activation of PKB signaling by PDK1.

Similarly, PDK1 kinase inhibitors are useful for treating cancer or other proliferative disorders by blocking the activation of p70S6K by PDK1. There are several substrates of p70S6K, such as ribosomal S6 protein, eIF4B, PDCD4 etc., that are involved in translation inhibition complex formation or ribosomal protein synthesis. Inhibition of protein synthesis via inhibition of phosphorylation of ribosomal S6 protein is believed to inhibit the proliferation of tumor cells by mTOR inhibitors (e.g., rapamycin). p70S6K gene amplification has been observed in breast tumor specimens, Simultaneous amplification of p70S6K and HER-2 correlates with poor survival in cancer patients. Hyperactivation of p70S6K (as measured by phosphorylation of T389) has been observed by immunohistochemical analysis of breast, head and neck squamous cell carcinoma (HNSCC), glioblastoma, lung and liver primary tumor specimens.

Likewise, PDK1 kinase inhibitors are useful for the treatment of cancer by blocking the activation of RSK1 (also known as p90RSK) by PDK1. RSK1 transduces anti-apoptotic and proliferative signals be mediating phosphorylation directly or indirectly of BAD, LKB1, TSC2, NFkB, mTOR. Ras/MAPK pathway is activated in >50% in primary tumors. RSK1 activity is correlated with MAPK activity. RSK1 is overexpressed in primary breast and prostate cancer samples.

PDK1 signaling regulates multiple critical steps in angiogenesis. Inhibitors of the activity of PDK1 are thus useful in the treatment of cancer, in particular cancers associated with deregulated activity of the PTEN/PI3K pathway including, but not limited to PTEN loss of function mutations, PI3K gain of function mutations and receptor tyrosine kinase gain of function mutations, PDK1 signaling has also been implicated in tumorigenesis and a PDK1 inhibitor is useful for tumor prevention or prevention of tumor recurrence. Mice with a PTEN heterozygous (PTEN$^{+/-}$) genotype are well-known to spontaneously develop tumors. Alessi and co-workers found that PDK1 hypomorphic PTEN$^{+/-}$ mice expressing <30% of normal PDK1 protein levels showed a significant delay in tumor formation as compared to littermate controls expressing normal levels of PDK1 protein (Current Biology, 2005, 15, 1839-1846).

SGK1 (serum and glucocorticoid-regulated kinase-1) activity is critical for insulin-mediated Na+ retention and hypertensive effects. Inhibition of SGK1 activity by a PDK1 kinase inhibitor is useful in treating hypertension and/or hypoinsulinemia.

The compounds of the instant invention are useful for treating tumor recurrence.

The compounds of the instant invention are useful for treating hypertension.

The compounds of the instant invention are useful for treating diabetes mellitus.

The instant invention provides a method for treating tumor recurrence that comprises administering such inhibitors of PDK1 activity.

The instant invention provides a method for treating hypertension that comprises administering such inhibitors of PDK1 activity.

The instant invention provides a method for treating diabetes mellitus that comprises administering such inhibitors of PDK1 activity.

The compounds, compositions and methods provided herein are particularly deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

Cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

Cancers that may be treated by the compounds, compositions and methods of the invention include breast, prostate, colon, ovary, endometrium and thyroid.

Cancers that may be treated by the compounds, compositions and methods of the invention include breast and prostate.

The compounds of the invention are also useful in preparing a medicament that is useful in treating cancer.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

The compounds of the instant invention are useful for treating cancer in combination with taxanes.

The compounds of the instant invention are useful for treating cancer in combination with docetaxel (Taxotere®).

The compounds of the instant invention are useful for treating cancer in combination with vorinostat (Zolinza®).

The compounds of the instant invention are useful for treating cancer in combination with the mTor inhibitor, AP 23573.

The compounds of the instant invention are useful for treating cancer in combination with the IGF1R inhibitor, MK-0646.

The compounds of the instant invention are useful for treating cancer in combination with satraplatin.

The compounds of the instant invention are useful for treating cancer in combination with lapatinib (Tykerb®).

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

In an embodiment, a suitable amount of an inhibitor of PDK1 is administered to a mammal undergoing treatment for cancer. Administration occurs in an amount of inhibitor of between about 0.1 mg/kg of body weight to about 60 mg/kg of body weight per day, or between 0.5 mg/kg of body weight to about 40 mg/kg of body weight per day. Another therapeutic dosage that comprises the instant composition includes from about 0.01 mg to about 1000 mg of inhibitor of PDK1. In another embodiment, the dosage comprises from about 1 mg to about 1000 mg of inhibitor of PDK1.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

All patents, publications and pending patent applications identified are hereby incorporated by reference.

Abbreviations used in the description of the chemistry and in the Examples that follow are: BSA (bovine serum albumin); BOC (tert-butylcarbonate); BOC$_2$O (di-tert-butyl dicarbonate); CDCl$_3$ (chloroform-d); CDI (1,1'-carbonyldiimidazole); C$_2$D$_6$SO (dimethyl sulfoxide-d6); CH$_2$Cl$_2$ (dichloromethane); CH$_3$OH (methanol); CO$_2$ (carbon dioxide); DIPEA (diisopropylethylamine); DMA (N,N-dimethylacetamide); DMF (N,N-dimethylformamide); DMSO (dimethyl sulfoxide); DTT (dithiothreitol); EDTA (ethylenediamine-tetra-acetic acid); EGTA (ethylene-glycol-tetra-acetic acid); Et (ethyl); EtOAc (ethyl acetate); EtOH (ethanol); ESI (electrospray ionization); Fe (iron metal); HATU (O-(7-azabenzotriazol-1-yl)-N,N,N',N'-tetramethyluronium hexafluorophosphate); HCl (hydrochloric acid/hydrochloride salt); HPLC (high-performance liquid chromatography); LC-MS (liquid chromatography-mass spectrometry); LRMS (low resolution mass spectrum); MeOH (methanol); MgCl$_2$ (magnesium chloride); MW (molecular weight); NaCl (sodium chloride); NaF (sodiumk fluoride); NaH (sodium hydride); NaHCO$_3$ (sodium bicarbonate); NaOH (sodium hydroxide); Na$_2$SO$_4$ (sodium sulfate); NH$_4$Cl (ammonium chloride); NMP (1-methyl-2-pyrrolidinone); NMR (nuclear magnetic resonance); PBS (phosphate buffered saline); RBF (round-bottomed flask); RT (room temperature); TFA (trifluoroacetic acid); THF (tetrahydrofuran); Zn (zinc metal) and μW (microwave irradiation).

The compounds of this invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of Formula A hereinabove.

Reactions used to generate the compounds of this invention are prepared by employing reactions as shown in Reaction Schemes 1-7.

Synopsis of Reaction Schemes

Reaction Scheme 1

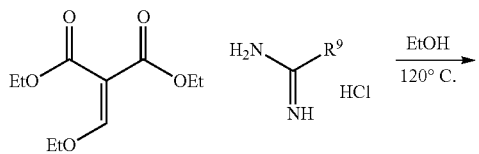

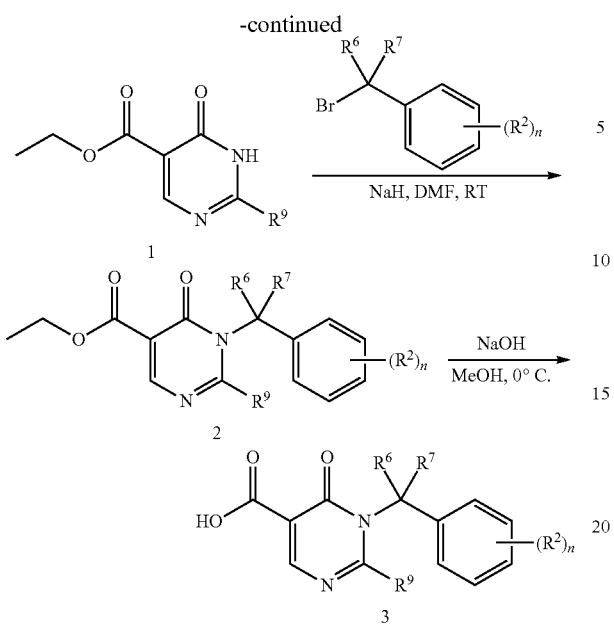

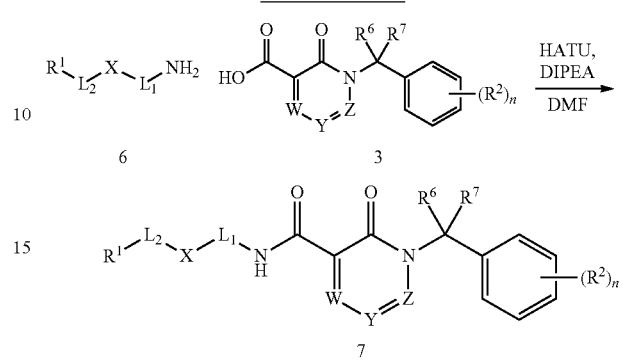

Reaction Scheme 1 shows the route to obtain carboxylic acids 3. The pyrimidone 1 is formed by cyclization of diethyl ethoxymethylenemalonate with imidamides in ethanol with acid. Pyrimidone 1 is then alkylated with benzyl bromides to produce intermediates 2. The ethyl esters 2 are then saponified with sodium hydroxide to produce acids 3.

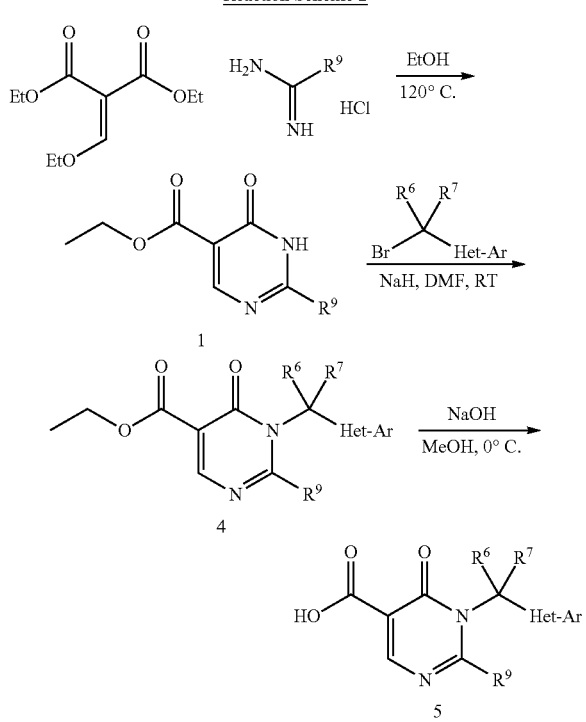

Reaction Scheme 2 shows the route to obtain carboxylic acids 5. The pyrimidone 1 is formed by cyclization of diethyl ethoxymethylenemalonate with imidamides in ethanol with acid. Pyrimidone 1 is then alkylated with heteroarylmethyl bromides to produce intermediates 4. The ethyl esters 4 are then saponified with sodium hydroxide to produce acids 5.

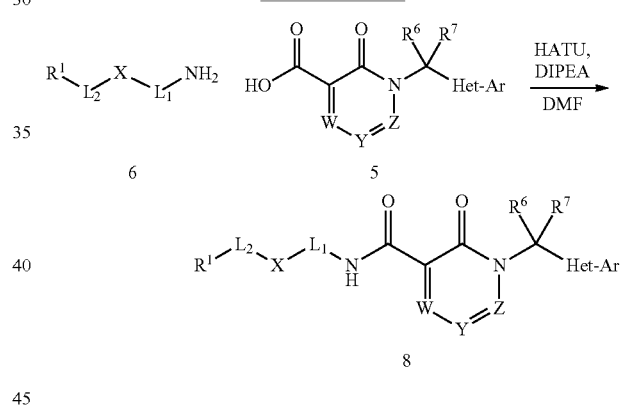

Reaction Scheme 3 shows the coupling of amines or amine salts 6 and carboxylic acids 3 via the action of a coupling agent such as HATU to produce amides 7.

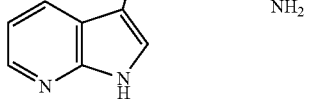

Reaction Scheme 4 shows the coupling of amines or amine salts 6 and carboxylic acids 5 via the action of a coupling agent such as HATU to produce amides 8.

Synthesis of the following amines (either as freebase of as a salt of either HCl or TFA) of formula $R^1$-$L_2$-X-$L_1$-$NH_2$ in Table 1 were described in WO2008/005457. The amines or amine salts in Table 1 can be used as substrates in the reactions described in Reaction Scheme 3 and Reaction Scheme 4 to provide amides 7 and 8:

TABLE 1

| Entry | Amine |
|---|---|
| 1 | |

TABLE 1-continued
| Entry | Amine |
|---|---|
| 2 | |
| 3 | |
| 4 | |
| 5 | |
| 6 | |
| 7 | |
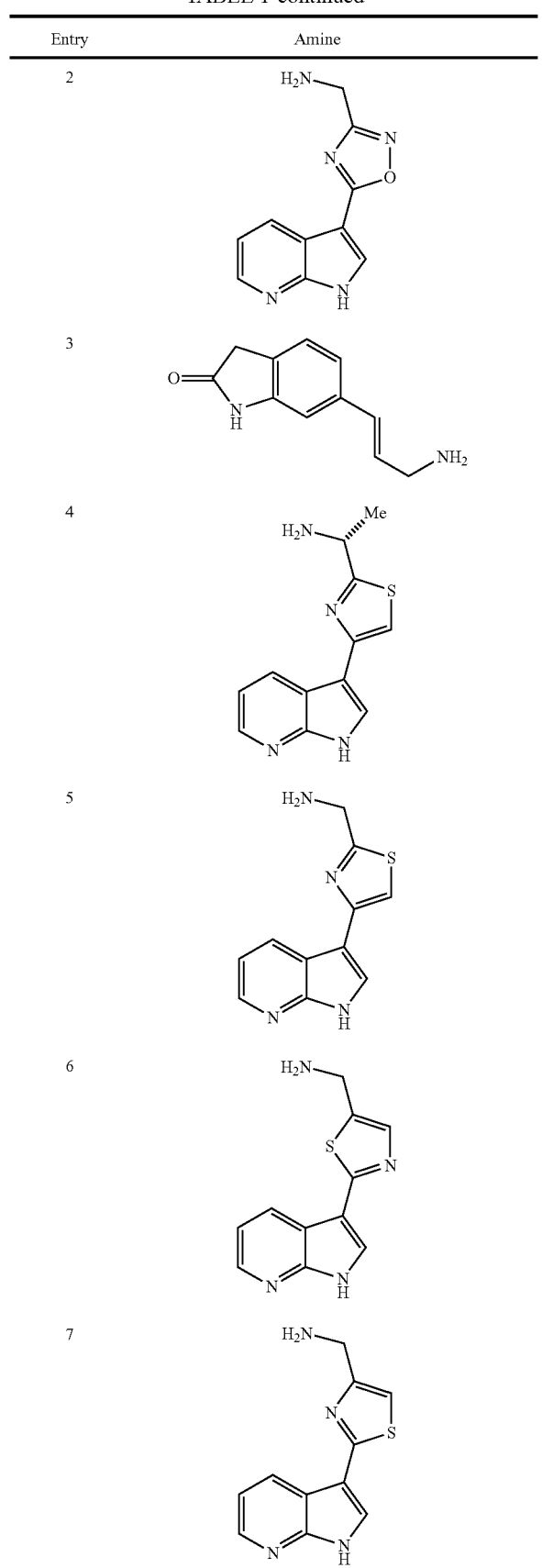
TABLE 1-continued
| Entry | Amine |
|---|---|
| 8 | |
| 9 | |
| 10 | |
| 11 | |
| 12 | |
| 13 | |
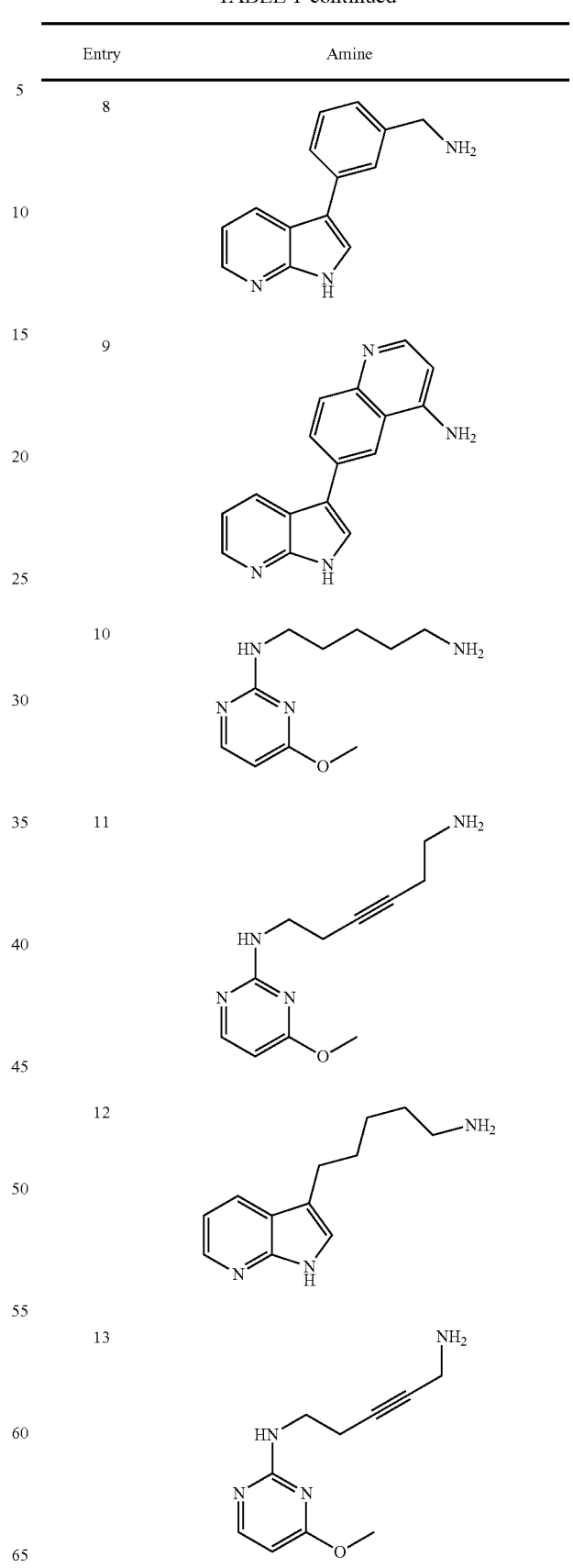

TABLE 1-continued
| Entry | Amine |
|---|---|
| 14 | 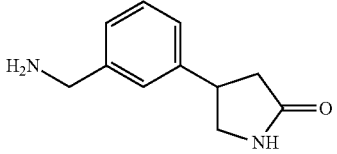 [SMILES: NCc1cccc(C2CNC(=O)C2)c1] |
| 15 | 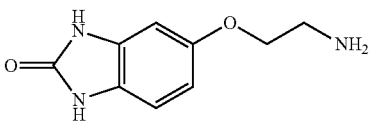 [SMILES: NCCOc1ccc2[nH]c(=O)[nH]c2c1] |
| 16 | 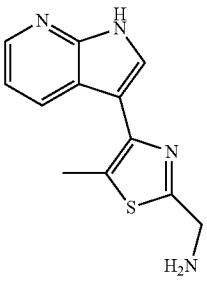 [SMILES: Cc1sc(CN)nc1-c1c[nH]c2ncccc12] |
| 17 | 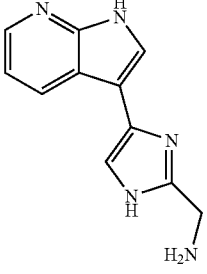 |
| 18 | 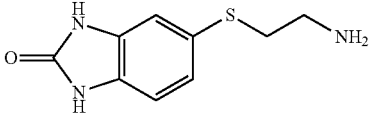 [SMILES: NCCSc1ccc2[nH]c(=O)[nH]c2c1] |
| 19 | 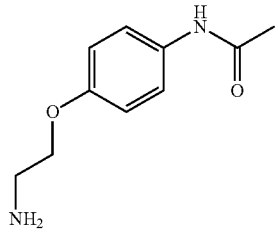 |
| 20 | 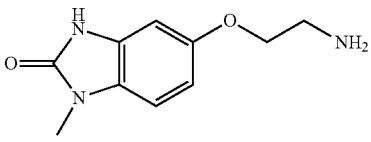 |
| 21 | 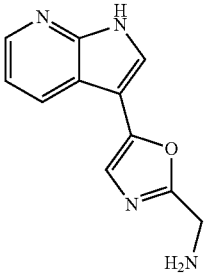 [SMILES: NCc1ncc(-c2c[nH]c3ncccc23)o1] |
| 22 | 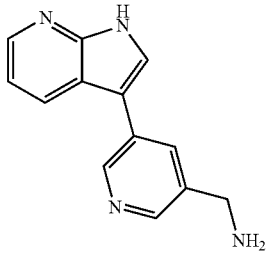 [SMILES: NCc1cncc(-c2c[nH]c3ncccc23)c1] |
| 23 | 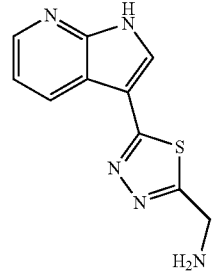 [SMILES: NCc1nnc(-c2c[nH]c3ncccc23)o1] |
| 24 | 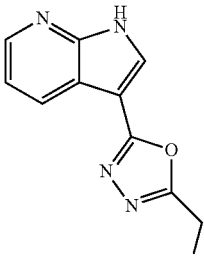 |
| 25 | 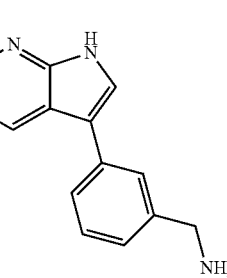 |
| 26 | 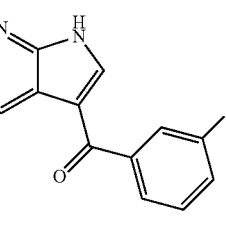 |

TABLE 1-continued

| Entry | Amine |
|---|---|
| 27 | (1H-pyrrolo[2,3-b]pyridin-3-ylmethyl)benzenamine |
| 28 | 3-(1H-pyrrolo[2,3-b]pyridin-3-yl)-1,2,4-oxadiazol-5-yl)methanamine |
| 29 | 5-(2-aminoethoxy)-3-(2-(pyrrolidin-1-yl)ethyl)-1H-benzo[d]imidazol-2(3H)-one |
| 30 | (2-(1H-pyrrolo[2,3-b]pyridin-3-yl)oxazol-4-yl)methanamine |
| 31 | 1-(5-(1H-pyrrolo[2,3-b]pyridin-3-yl)-1,3,4-oxadiazol-2-yl)cyclopropanamine |
| 32 | 1-(4-(1H-pyrrolo[2,3-b]pyridin-3-yl)thiazol-2-yl)cyclopropanamine |
| 33 | (5-((1H-pyrrolo[2,3-b]pyridin-3-yl)methyl)thiazol-2-yl)methanamine |
| 34 | 5-(2-amino-3-fluorophenoxy)-1H-benzo[d]imidazol-2(3H)-one |
| 35 | methyl 2-amino-3-((2-oxo-2,3-dihydro-1H-benzo[d]imidazol-5-yl)oxy)propanoate |
| 36 | (5-(1H-pyrrolo[2,3-b]pyridin-3-yl)-1H-pyrazol-3-yl)methanamine |
| 37 | 5-(2-amino-2-(4-fluorophenyl)ethoxy)-1H-benzo[d]imidazol-2(3H)-one |

TABLE 1-continued
| Entry | Amine |
|---|---|
| 38 | 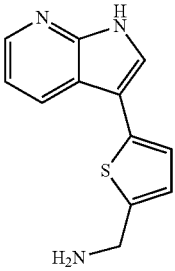 [SMILES: NCc1ccc(-c2c[nH]c3ncccc23)s1] |
| 39 | 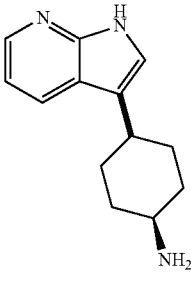 |
| 40 | 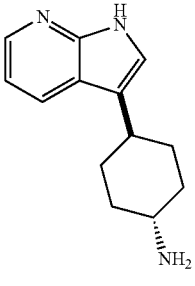 |
| 41 | 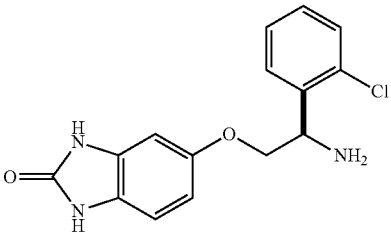 [SMILES: N[C@@H](COc1ccc2[nH]c(=O)[nH]c2c1)c1ccccc1Cl] |
| 42 | 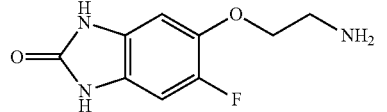 [SMILES: NCCOc1cc2[nH]c(=O)[nH]c2cc1F] |
| 43 | 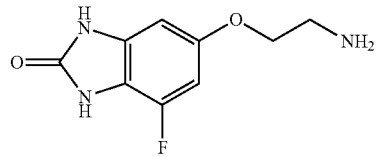 [SMILES: NCCOc1cc(F)c2[nH]c(=O)[nH]c2c1] |
| 44 | 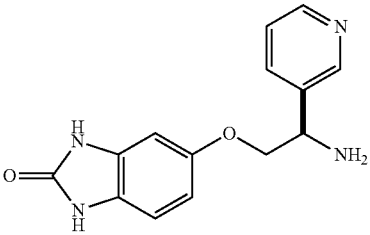 [SMILES: N[C@@H](COc1ccc2[nH]c(=O)[nH]c2c1)c1cccnc1] |
| 45 | 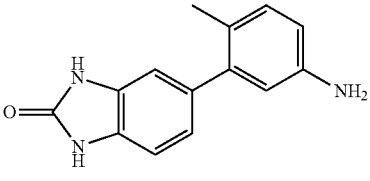 [SMILES: Cc1ccc(N)cc1-c1ccc2[nH]c(=O)[nH]c2c1] |
| 46 | 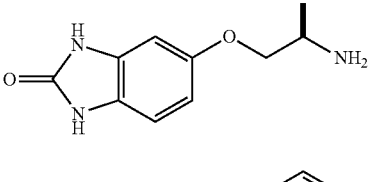 |
| 47 | 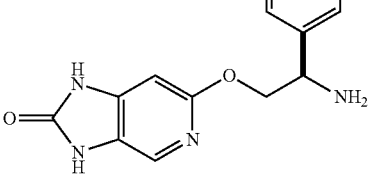 |
| 48 | 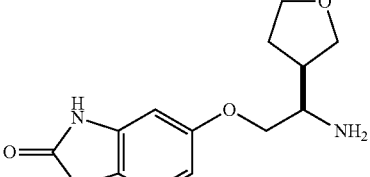 |
| 49 | 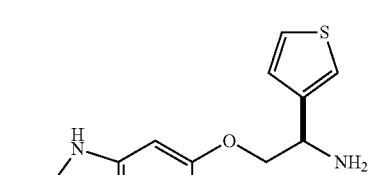 |
| 50 | 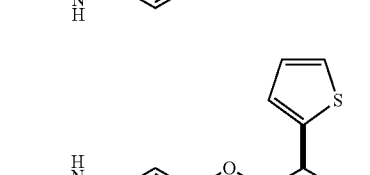 |

TABLE 1-continued

| Entry | Amine |
|---|---|
| 51 | 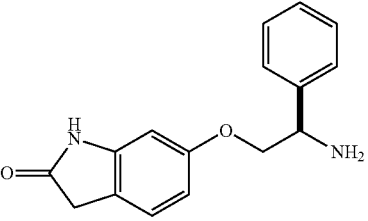 [SMILES: N[C@@H](COc1ccc2c(c1)NC(=O)C2)c1ccccc1] |

Reaction Scheme 5

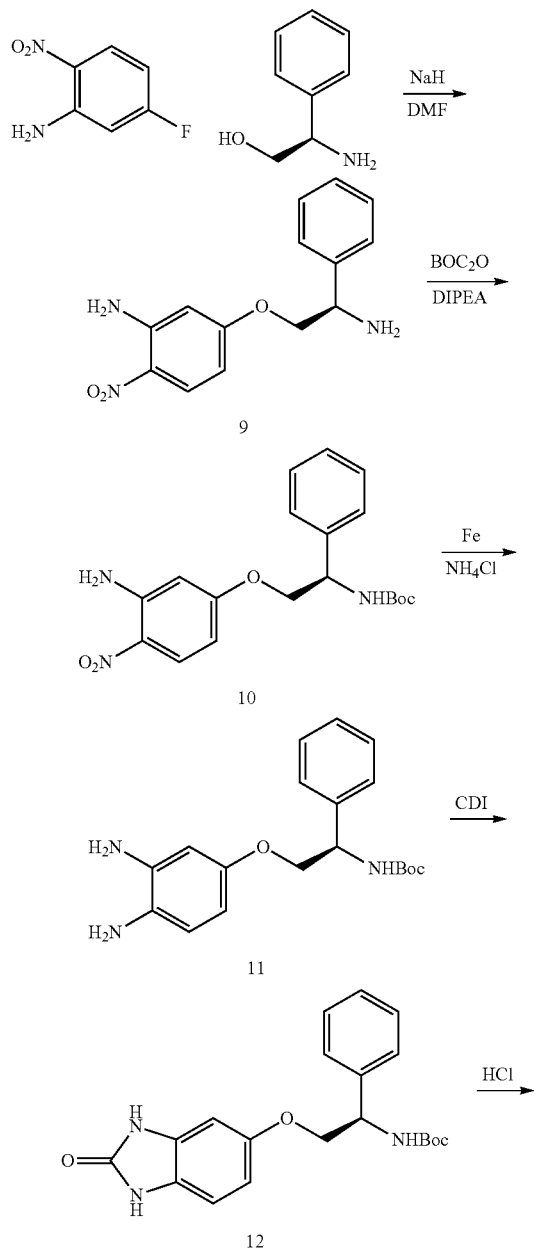

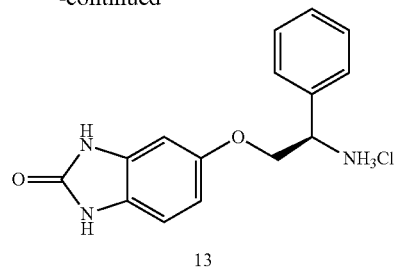

Reaction Scheme 5 shows the synthesis of amine 13 starting from D-phenylglycinol. Following $S_NAr$ displacement of fluoride from 5-fluoro-2-nitroaniline by D-phenylglycinol to afford 9, BOC protection of amine to afford 10, reduction with iron/ammonium chloride afforded bis-aniline 11 that was subsequently cyclized by the action of CDI to afford penultimate urea 12. BOC-protected urea 12 was then deprotected using HCl to provide the hydrochloride salt of amine 13.

Reaction Scheme 6

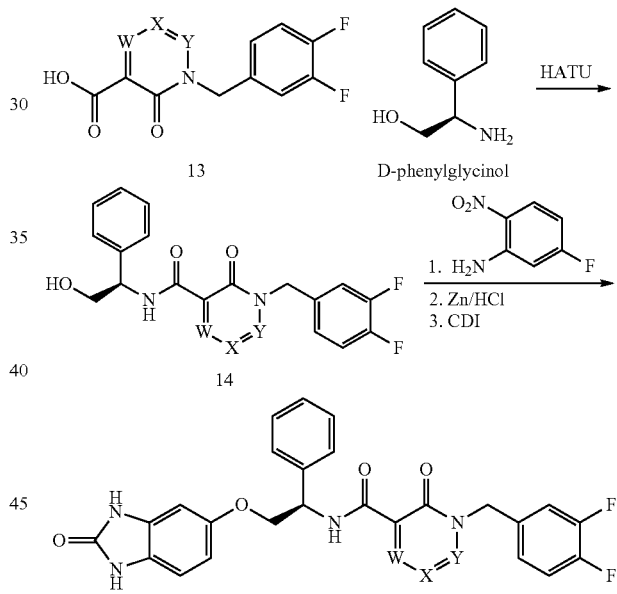

Reaction Scheme 6 shows a method for the preparation of compounds 15. Coupling acids 13 to D-phenylglycinol using HATU provided alcohols 14 that were then coupled via an $S_NAr$ reaction to 4-nitro-3-amino-fluorobenzene and subsequently reduced with Zn and HCl and underwent cyclic urea formation with CDI to provide compounds 15.

INTERMEDIATE 1

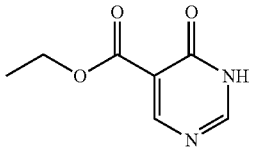

ethyl 6-oxo-1,6-dihydropyrimidine-5-carboxylate

A mixture of formamidine hydrochloride (4.02 g, 49.9 mmol) and diethyl ethoxymethylenemalonate (5 ml, 24.95 mmol) in ethanol (4.99 ml) was heated to 120° C. (by microwave irradiation) for 15 h. After the reaction mixture was cooled to room temperature, ethyl acetate, hydrochloric acid (1M), and water were added. The aqueous layer was washed with ethyl acetate and then extracted with 3:1 chloroform:isopropanol. The combined organic extracts were dried over magnesium sulfate and concentrated under reduced pressure to afford ethyl 6-oxo-1,6-dihydropyrimidine-5-carboxylate as an orange solid. LRMS (ESI) calc'd for ($C_7H_9N_2O_3$) [M+H]$^+$, 169.1; found 169.1.

INTERMEDIATE 2

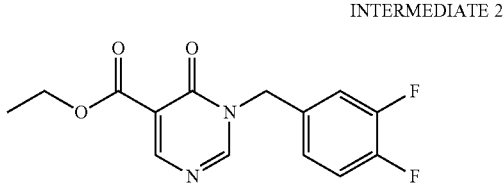 [SMILES: CCOC(=O)c1cncn(Cc2ccc(F)c(F)c2)c1=O]

ethyl 1-(3,4-difluorobenzyl)-6-oxo-1,6-dihydropyrimidine-5-carboxylate

A mixture of sodium hydride (0.262 g, 6.54 mmol, 60% dispersion in mineral oil) and ethyl 6-oxo-1,6-dihydropyrimidine-5-carboxylate (1 g, 5.95 mmol) was dissolved in DMF (11.89 ml). After 30 min at room temperature, 3,4-difluorobenzyl bromide (0.761 ml, 5.95 mmol) was added. The reaction mixture was stirred at room temperature overnight and then poured into aqueous hydrochloric acid (10%). The aqueous layer was extracted with ethyl acetate. The combined organic extracts were washed with brine, dried over sodium sulfate, and concentrated under reduced pressure. The residue was purified by column chromatography on silica gel, eluting with ethyl acetate/hexanes, to afford ethyl 1-(3,4-difluorobenzyl)-6-oxo-1,6-dihydropyrimidine-5-carboxylate as an off-white solid. LRMS (EST) calc'd for ($C_{14}H_{13}F_2N_2O_3$) [M+H]$^+$, 295.1; found 295.1.

INTERMEDIATE 3

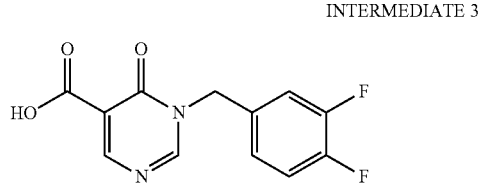 [SMILES: O=C(O)c1cncn(Cc2ccc(F)c(F)c2)c1=O]

1-(3,4-difluorobenzyl)-6-oxo-1,6-dihydropyrimidine-5-carboxylic acid

To a solution of ethyl 1-(3,4-difluorobenzyl)-6-oxo-1,6-dihydropyrimidine-5-carboxylate (470 mg, 1.597 mmol) in methanol (3195 µl) at 0° C., aqueous sodium hydroxide (1917 µl, 1.917 mmol, 1M) was added dropwise. After warming to room temperature over 2 h, the reaction mixture was concentrated under reduced pressure. To the residue, water (5 mL) and ethyl acetate (2.5 mL) were added. The aqueous layer was washed with ethyl acetate and then acidified to pH 1 with aqueous hydrochloric acid (1M). The aqueous layer was then extracted with ethyl acetate. The combined organic extracts were washed with water and brine, dried over magnesium sulfate, and concentrated under reduced pressure to afford 1-(3,4-difluorobenzyl)-6-oxo-1,6-dihydropyrimidine-5-carboxylic acid as a white solid. LRMS (ESI) calc'd for ($C_{12}H_9F_2N_2O_3$) [M+H]$^+$, 267.1; found 267.0.

INTERMEDIATE 4

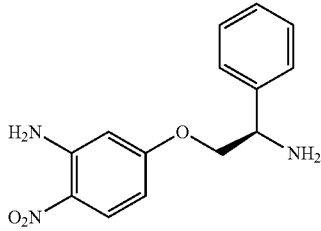

5-[(2R)-2-amino-2-phenylethoxy]-2-nitroaniline (R)-(−)-2-Phenylglycinol (5.043 g, 36.8 mmol) was placed in a 250-mL RBF and placed under a nitrogen atmosphere. DMF (100 mL) was added and the reaction was stirred until a clear, colourless solution resulted. NaH (2.206 g, 55.1 mmol) was then added, followed by DMF (10 mL) as a wash, producing a vigorous reaction (gas evolution). The reaction was stirred at room temperature until the gas evolution had subsided, leaving a reddish heterogeneous mixture. 5-Fluoro-2-nitroaniline (6.89 g, 44.1 mmol) was then added, followed by DMF (10 mL), which immediately produced a bright red colour. The reaction was left stirring at room temperature and monitored by LC-MS. The reaction was quenched by its addition to an Erlenmeyer flask containing ethyl acetate (200 mL) and dilute aqueous NaHCO$_3$ (250 mL). The phases were separated in a separatory funnel, and the organic layer was washed with water (150 mL), then brine (100 mL), dried over anhydrous Na$_2$SO$_4$ and concentrated in vacuo. The reaction was then purified by silica gel column (5-75% EtOAc in n-heptane), yielding two fractions of high purity 5-[(2R)-2-amino-2-phenylethoxy]-2-nitroaniline, both contaminated with residual DMF, as a yellow-orange oil. LRMS (ESI) calc'd for ($C_{14}H_{16}N_3O_3$) [M+H]$^+$, 274.1; found 274.1.

INTERMEDIATE 5

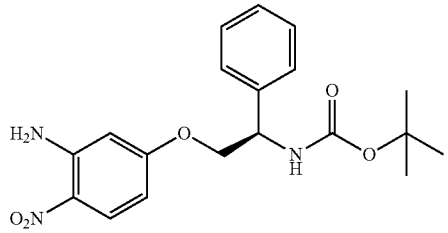

tert-butyl [(1R)-2-(3-amino-4-nitrophenoxy)-1-phenylethyl]carbamate

5-[(2R)-2-Amino-2-phenylethoxy]-2-nitroaniline (Intermediate 4) (2.35 g, 8.60 mmol) was placed in a 100-mL RBF under a nitrogen atmosphere, followed by THF (30 mL). N,N-diisopropylethylamine (2.25 mL, 12.9 mmol) was added, the reaction was stirred for ten minutes, followed by the addition of di-tert-butyl dicarbonate (2.40 mL, 10.3 mmol). The reaction was then stirred at room temperature for three hours, and then analyzed by LC-MS, which showed the reaction to be complete. The reaction was added to a separatory funnel containing ethyl acetate (300 mL) and dilute aqueous NaHCO$_3$ (150 mL); the phases were separated and the organic layer was washed with brine (100 mL), dried over anhydrous Na$_2$SO$_4$ and concentrated in vacuo, affording tert-butyl [(1R)-2-(3-amino-4-nitrophenoxy)-1-phenylethyl]carbamate as a yellow solid. LRMS (ESI) calc'd for (C$_{19}$H$_{23}$N$_3$NaO$_5$) [M+Na]$^+$, 396.2; found 396.2.

INTERMEDIATE 6

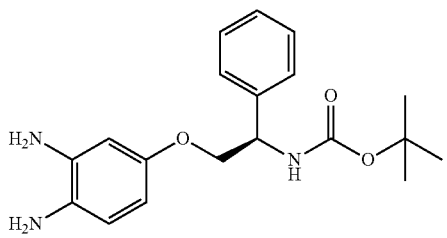

tert-butyl [(1R)-2-(3,4-diaminophenoxy)-1-phenylethyl]carbamate tert-Butyl [(1R)-2-(3-amino-4-nitrophenoxy)-1-phenylethyl]carbamate (Intermediate 5) (346 mg, 0.93 mmol) was placed in a microwave reaction vial (10-20 mL), followed by iron (259 mg, 4.63 mmol), water (4 mL), ammonium chloride (40 mg, 0.74 mmol) and finally ethanol (4 mL). The reaction vial was sealed, and set to heat at 80° C. for twenty hours. The reaction was added to a separatory funnel containing ethyl acetate (100 mL) and brine (75 mL); the phases were separated, and the organic layer was washed again with brine (75 mL). The ethyl acetate layer was then concentrated in vacuo to afford tert-butyl [(1R)-2-(3,4-diaminophenoxy)-1-phenylethyl]carbamate as an orange solid. LRMS (ESI) calc'd for (C$_{19}$H$_{26}$N$_3$O$_3$) [M+H]$^+$, 344.2; found 344.2.

INTERMEDIATE 7

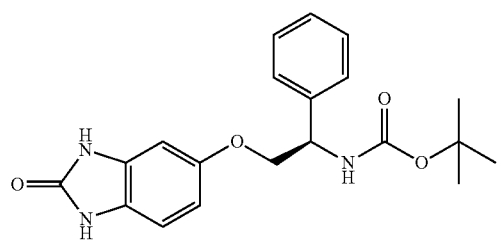

tert-butyl {(1R)-2-[(2-oxo-2,3-dihydro-1H-benzimidazol-5-yl)oxy]-1-phenylethyl}carbamate tert-Butyl [(1R)-2-(3,4-diaminophenoxy)-1-phenylethyl] carbamate (Intermediate 6) (318 mg, 0.93 mmol) was placed in a 50-mL RBF under a nitrogen atmosphere and dissolved in DMF (5 mL). CDI (135 mg, 0.83 mmol) was added, and the reaction was stirred at room temperature for four hours. The reaction was added to a separatory funnel containing ethyl acetate (125 mL) and dilute aqueous NaHCO$_3$ (75 mL); the phases were separated, and the organic layer was washed with brine (75 mL), dried over anhydrous Na$_2$SO$_4$ and then concentrated in vacuo. The crude product mixture was then purified by silica gel chromatography to afford tert-butyl {(1R)-2-[(2-oxo-2,3-dihydro-1H-benzimidazol-5-yl)oxy]-1-phenylethyl}carbamate as a white solid. $^1$H NMR (500 MHz, C$_2$D$_6$SO) δ 10.49 (s, 1H), 10.37 (s, 1H), 7.54 (d, 1H), 7.34 (m, 4H), 7.25 (t, 1H), 6.77 (d, 1H), 6.48 (s, 2H), 4.86 (q, 1H), 3.98 (m, 2H), 1.37 (s, 9H). LRMS (ESI) calc'd for (C$_{16}$H$_{16}$N$_3$O$_4$) [M−C$_4$H$_8$+H]$^+$, 314.1; found 314.1.

INTERMEDIATE 8

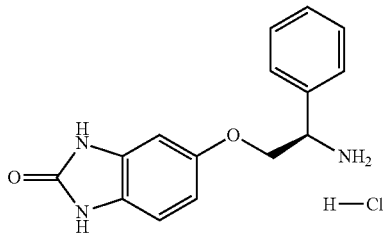

5-[(2R)-2-amino-2-phenylethoxy]-1,3-dihydro-2H-benzimidazol-2-one hydrochloride tert-Butyl {(1R)-2-[(2-oxo-2,3-dihydro-1H-benzimidazol-5-yl)oxy]-1-phenylethyl}carbamate (Intermediate 7) (67 mg, 0.18 mmol) was placed in a 10-mL RBF under a nitrogen atmosphere and dissolved in THF (2 mL). HCl (1 mL, 4.0 mmol) (4M in 1,4-dioxane) was added, and the reaction was stirred at room temperature for sixteen hours. The reaction then concentrated in vacuo, with repeated cycles of dilution/concentration with THF to minimize the residual HCl, to afford 5-[(2R)-2-amino-2-phenylethoxy]-1,3-dihydro-2H-benzimidazol-2-one hydrochloride as a yellow solid. LRMS (ESI) calc'd for (C$_{15}$H$_{16}$N$_3$O$_2$) [M+H]+, 270.1. found 270.1.

Reaction Scheme 7

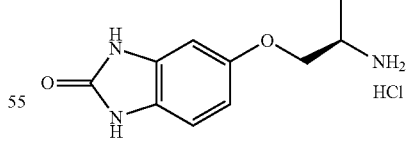

8

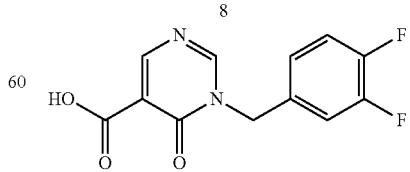

HATU, DIPEA
DMA, RT

3

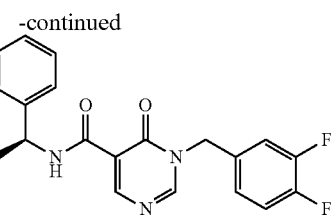

Example #1

Reaction Scheme 7 shows the coupling of amine salt 8 and carboxylic acid 3 to produce amide EXAMPLE #1.

Example #1

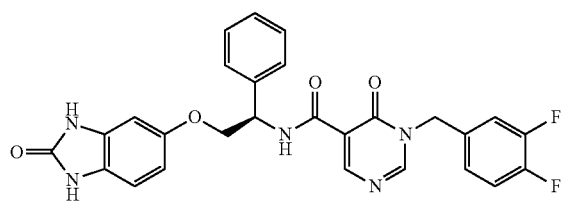 [SMILES: O=C(N[C@@H](COc1ccc2[nH]c(=O)[nH]c2c1)c1ccccc1)c1nccn(Cc2ccc(F)c(F)c2)c1=O]

1-(3,4-difluorobenzyl)-6-oxo-N-{(1R)-2-[(2-oxo-2,3-dihydro-1H-benzimidazol-5-yl)oxy]-1-phenylethyl}-1,6-dihydropyrimidine-5-carboxamide To a solution of 5-[(2R)-2-amino-2-phenylethoxy]-1,3-dihydro-2H-benzimidazol-2-one hydrochloride (38 mg, 0.124 mmol), 1-(3,4-difluorobenzyl)-6-oxo-1,6-dihydropyrimidine-5-carboxylic acid (33.1 mg, 0.124 mmol) and N,N-diisopropylethylamine (65.1 µl, 0.373 mmol) in DMA (710 µl), O-(7-azabenzotriazol-1-yl)-N,N,N',N'-tetramethyluronium hexafluorophosphate (54.3 mg, 0.143 mmol) was added. After stirring for 90 minutes at room temperature, the reaction mixture was diluted with water, acetonitrile, and DMSO. This solution was purified by preparative HPLC Reverse phase (C-18), eluting with Acetonitrile/Water+0.05% TFA, to afford 1-(3,4-difluorobenzyl)-6-oxo-N-{(1R)-2-[(2-oxo-2,3-dihydro-1H-benzimidazol-5-yl)oxy]-1-phenylethyl}-1,6-dihydropyrimidine-5-carboxamide as a white solid after neutralization, extraction, and drying of HPLC fractions. $^1$H NMR (500 MHz, C$_2$D$_6$SO) δ 10.51 (s, 1H), 10.38 (s, 1H), 9.73 (d, 1H), 8.95 (s, 1H), 8.67 (s, 1H), 7.52 (m, 1H), 7.41 (m, 3H), 7.34 (t, 2H), 7.25 (m, 2H), 6.74 (d, 1H), 6.49 (d, 2H), 5.36 (m, 1H), 5.19 (t, 2H), 4.26 (m, 1H), 4.19 (m, 1H). LRMS (ESI) calc'd for (C$_{27}$H$_{22}$F$_2$N$_5$O$_4$) [M+H]$^+$, 518.2; found 518.1.

INTERMEDIATE 9

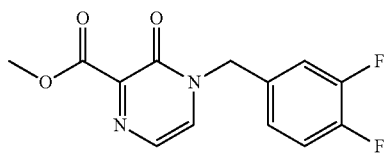

methyl 4-(3,4-difluorobenzyl)-3-oxo-3,4-dihydropyrazine-2-carboxylate

Methyl 2-hydroxy-3-pyrazinecarboxylate (103 mg, 0.67 mmol) (obtained from Fulcrum Scientific Ltd.) was placed in a 25-mL RBF and placed under a nitrogen atmosphere. DMF (3 mL) was added, followed by NaH (33 mg, 0.83 mmol) and the reaction was allowed to stir for twenty minutes at room temperature. 3,4-Difluorobenzyl bromide (0.094 mL, 0.735 mmol) was added, and the reaction was allowed to stir at room temperature overnight, and the reaction was found to be complete by LC-MS. The reaction was added to a separatory funnel containing ethyl acetate (125 mL) and dilute aqueous NaHCO$_3$ (75 mL); the phases were separated and the organic layer was washed with brine and dried over anhydrous Na$_2$SO$_4$, then concentrated in vacuo. The crude product was purified by silica gel chromatography using 10-100% EtOAc in n-heptane to afford methyl 4-(3,4-difluorobenzyl)-3-oxo-3,4-dihydropyrazine-2-carboxylate as a yellow solid. $^1$H NMR (500 MHz, C$_2$D$_6$SO) δ 8.08 (d, 1H), 7.49 (t, 1H), 7.44 (d, 1H), 7.42 (t, 1H), 7.23 (m, 1H), 5.09 (s, 2H), 3.80 (s, 3H). LRMS (ESI) calc'd for (C$_{13}$H$_{11}$F$_2$N$_2$O$_3$) [M+H]$^+$, 281.1; found 281.1.

INTERMEDIATE 10

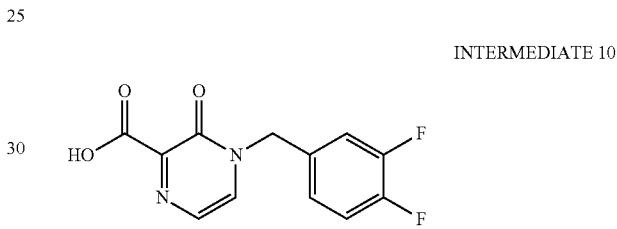

4-(3,4-difluorobenzyl)-3-oxo-3,4-dihydropyrazine-2-carboxylic acid

Methyl 4-(3,4-difluorobenzyl)-3-oxo-3,4-dihydropyrazine-2-carboxylate (110 mg, 0.39 zmol) was placed in a 10-mL RBF and dissolved in THF (3 mL). NaOH (1 mL, 2.000 mmol) (2N solution) was added, and the reaction was allowed to stir at room temp. The reaction was then left stirring overnight at room temp and then analyzed by LC-MS, showing the reaction to be complete. The reaction was then neutralized with the addition of 1N HCl (2 mL), and then saturated with saturated sodium chloride. The resultant mixture was then washed with ethyl acetate (3×50 mL), and then combined organic layers were washed with brine (25 mL) and concentrated in vacuo, affording 4-(3,4-difluorobenzyl)-3-oxo-3,4-dihydropyrazine-2-carboxylic acid as a yellow solid. LRMS (ESI) calc'd for (C$_{12}$H$_9$F$_2$N$_2$O$_3$) [M+H]$^+$, 267.1; found 267.0.

Example #2

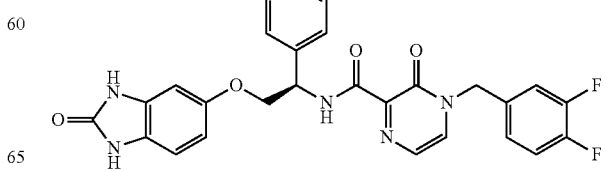

4-(3,4-difluorobenzyl)-3-oxo-N-{(1R)-2-[(2-oxo-2,3-dihydro-1H-benzimidazol-5-yl)oxy]-1-phenylethyl}-3,4-dihydropyrazine-2-carboxamide 4-(3,4-Difluorobenzyl)-3-oxo-3,4-dihydropyrazine-2-carboxylic acid (48 mg, 0.18 mmol) was placed in a 25-mL RBF under a nitrogen atmosphere followed by HATU (82 mg, 0.22 mmol), then NMP (1.0 mL) and finally N,N-diisopropylethylamine (0.11 mL, 0.63 mmol). The reaction was stirred for five minutes at room temperature, and was added to a solution of 5-[(2R)-2-amino-2-phenylethoxy]-1,3-dihydro-2H-benzimidazol-2-one (55 mg, 0.18 mmol) in NMP (1.0 mL). The reaction was allowed to stir at room temperature for forty minutes, then was added to a separatory funnel containing ethyl acetate (75 mL) and dilute aqueous $NH_4Cl$ (50 mL); the phases were separated and the organic layer was washed with saturated aqueous $NaHCO_3$ (50 mL), followed by brine (50 mL) and dried over anhydrous $Na_2SO_4$, then concentrated in vacuo. The crude product was purified by silica gel chromatography (10-gram column) using 0-10% $CH_3OH$ in $CH_2Cl_2$, with the product eluting at 8% $CH_3OH$ in $CH_2Cl_2$, to afford 4-(3,4-difluorobenzyl)-3-oxo-N-{(1R)-2-[(2-oxo-2,3-dihydro-1H-benzimidazol-5-yl)oxy]-1-phenylethyl}-3,4-dihydropyrazine-2-carboxamide as a light yellow solid. $^1$H NMR (500 MHz, $C_2D_6SO$) δ 10.51 (s, 1H), 10.38 (s, 1H), 9.82 (d, 1H), 8.05 (d, 1H), 7.57 (d, 1H), 7.50 (m, 1H), 7.43 (m, 3H), 7.35 (t, 2H), 7.27 (t, 1H), 7.24 (m, 1H), 6.75 (d, 1H), 6.51 (d, 2H), 5.34 (m, 1H), 5.16 (s, 2H), 4.09 (m, 2H). LRMS (ESI) calc'd for $(C_{27}H_{23}F_2N_5O_4)$ [M+H]$^+$, 518.2; found 518.2.

Compounds of this invention were tested in the following biological assay and were found to have $IC_{50}$ values of less than 30 μM.

Biological Assays

In Vitro PDK1 Kinase Assay

Activated recombinant full-length mT(Glu-Glu-Phe) tagged human PDK1 was used to determine whether the compounds of the instant invention modulate the enzymatic activity of this kinase.

The cDNA, encoding full-length PDK1, was subcloned into a baculovirus expression vector pBlueBac4.5 (Invitrogen), containing an in frame middle T tag (MEYMPME) at its N-terminus. Soluble activated recombinant full-length mT(Glu-Glu-Phe) tagged human PDK1 was expressed in a baculovirus-infected Sf9 insect cells (Kemp Biotechnologies), according to the protocol recommended by the manufacturer. Immunoaffinity purification of the PDK1 kinase from the insect cell lysate was performed using a middle Tag antibody bound to Protein G-EE column. Upon elution using 50 mM Tris pH 7.4, 1 mM EDTA, 1 mM EGTA, 0.5 mM $Na_3VO_4$, 1 mM DTT, 50 mM NaF, Na Pyrophospate, Na-β-glycerophosphate, 10% glycerol, Complete, 1 μM microcystein, and 50 μg/ml EYMPME peptide, fractions containing PDK1 protein were pooled together, based on SDS-PAGE and western blot analyses, and then analyzed for protein concentration using BCA Protein Assay (Pierce) with BSA as standard. The final product was aliquoted and flash frozen in liquid nitrogen before being stored at −80° C. Resulting PDK1 protein had MW of 64 kDa, was phosphorylated 'by default' and purified as an activated kinase from insect cells.

The procedure for determining the potency of a compound to inhibit PDK1 kinase comprises the following steps:
1. Prepare 3-fold serial diluted compound solutions in 100% dimethyl sulfoxide (DMSO) at 20× of the desired final concentrations in a 384-well plate.
2. Prepare a master reaction mix containing 62.5 mM HEPES (pH 7.5), 12.5 mM $MgCl_2$, 0.013% Brij-35, 1.25 mM EGTA, 2.5 mM dithiothreitol, 1.25 nM recombinant PDK1 and 375 nM biotinylated synthetic peptide substrate (Biotin-GGDGATMKTFCGGTPSDGDPDGGEFTEF-COOH) (SEQ. ID.: 1).
3. In a black assay plate, add 2.5 μl of compound solution (or DMSO) and 22.5 μl of master reaction mix per well. Pre-incubate for 10 min. Initiate the kinase reaction by adding 6 μl of 0.25 mM MgATP per well. Allow the reactions to proceed for 25 min at room temperature. The final conditions for the reaction are 1 nM PDK1, 300 nM peptide substrate, 5 μM MgATP, 10 mM $MgCl_2$, 2 mM DTT, 50 mM HEPES (pH 7.5), 0.01% Brij-35, 1 mM EGTA and 5% DMSO.
4. Stop the kinase reaction with 30 μl of Stop/Detection buffer containing 10 mM EDTA, 1× Lance Detection Buffer (cat. #CR97-100, PerkinElmer), 1% SuperBlocking in TBS (cat. #37535, Pierce), 5 nM phospho-Akt (T308) monoclonal antibody (cat. #4056, Cell Signaling Technologies), 5 nM Lance labeled Eu-Anti-rabbit IgG (cat. #AD0083, PerkinElmer), and 100 nM Streptavidin-allophycocyanin conjugate (cat. #PJ25S, Prozyme).
5. Read HTRF signals on an Envision reader (PerkinElmer) in HTRF mode after 60 min.
6. IC50 is determined by fitting the observed relationship between compound concentration and HTRF signal with a 4-parameter logistic equation.

Cell Biochemical Assay for PDK1 Inhibition
Objective:
To determine the inhibitory potency of PDK1 inhibitors (IC50) on the PI3'K pathway in PC3 cells using Odyssey Western Blot Analysis and a cocktail of Phosphospecific antibodies to two direct PDK1 substrates RSK (Ser221) and AKT (Thr308) and the downstream effector molecule S6RP (235/236).

Cells:
PC-3 cells grown in Earle's MEM with 10% FBS, 1× L-Glutamine, 1× Non Essential Amino Acids, 1× NaPyruvate and 1× Hepes. Other cells may be used.

Reagents:
Primary Antibodies:
P*Akt 308—Cell Signalling, Cat. #4056
P*RSKS221—Biosource Cat. #44 924G
P*S6RP235/236—Cell Signalling Cat #2211
P*-p44/42 MAP kinase (Thre202/Tyr204)—Cell signaling Cat. #9101
Total eIF4E—Cell signaling Cat. #9742
Secondary Antibody:
Infrared (IR)-labeled goat anti-mouse IRDye 600 (LI-COR Cat. #926-32221)
Infrared (IR)-labeled goat anti-rabbit IRDye 800CW (LI-COR Cat. #926-32210)
Reference Compounds (Pathway Inhibitors)
Rapamycin—Calbiochem, 553211
LY294002—Calbiochem, 440204
Protease Inhibitor Tablets—Roche 11836145001
PageRuler Prestained Protein Ladder—Fermentas, SM0671
Nitrocellulose Membrane
Buffers/Solutions
Lysis Stock (Store at 4° C.)
20 mM TrisHCl, pH 7.5
150 mM NaCl
15% Glycerol 1% Igepal
Complete Lysis Buffer
1.25 mL of 1M β-Glycerolphosphate
5 mL of 0.5M NaF
5 mL of 0.1M NaPPi
0.5 mL of 100 mM Sodium Orthovanadate
1 protease inhibitor tablet
Fill to 50 mL with Lysis Stock, make 10 mL aliquots and freeze. To one aliquot, add 100 uL of 200 mM PMSF before use.
TBS-Tween
20 mM TrisHCl, pH 7.5
150 mM NaCl
0.05% Tween-20
TBS
20 mM TrisHCl, pH 7.5
150 mM NaCl
Blocking Buffer
Odyssey Blocking Buffer (LI-COR, Cat. #927-40000)
Primary Diluent
4% BSA fraction5 in PBS
0.02% Tween-20
0.5% Sodium Azide
4×SDS Sample Buffer
Sample Protocol
Seed Cells 24 Hours Before Compound Stimulation in Full Growth Medium
1. Allow PC-3 cell growth in a T150 flask using standard tissue culture procedures until cells reach near confluence ($1.0 \times 10^7$).
2. Remove growth media, wash cells with sterile 1×PBS, and trypsinize cells for displacement using 3 ml Trypsin
3. Neutralize displaced cells with 30 ml of culture media and transfer to a 50 ml tube.
4. Vortex briefly the tube to resuspend and mix cell suspension thoroughly.
5. Count cells and dilute with media to a conc of 150,000 cells per mL.
6. Dispense 1 ml of the cell suspension to each well in a 12 well plate using a repeat pipetter and incubate for 24 hours in 37° C., 5% $CO_2$.
Compound Stimulation
1. Make a 3 fold dilution series of PDK1 inhibitors in DMSO using a 96 well master plate (7 different compound concentrations and a no compound DMSO control). Concentration should be 200× of the final conc used in the assay.
2. To stimulate cells, add 5 uL compound/DMSO to each well with cells and incubate for 24 hours in 37° C., 5% $CO_2$.
Cell Lysis
1. The following day, remove growth media, wash with cold 1×PBS and remove PBS completely before adding 100 uL of lysis buffer to each well.
2. Shake plates on shaker for 10 min in the cold room
3. Collect lysate from each well and transfer to 1.5 mL eppendorf tube standing on ice.
4. Spin down at 13,000 rpm at 4° C. for 5 min.
5. Transfer 90 uL of lysate into new eppendorf tube containing 30 uL of 4×SDS loading buffer.
6. Place tube in 70° C. heat block for 7 min and store sample at −80° C.
Western Blot Detection
1. Run samples on 18 well 10% or 4-20% Tris-Glycine Biorad gels (70V, constat 40 min) loading 30 uL sample per well and 2 uL pre-stained molecular weight marker. Load ladder in the first and ninth well
2. Blot onto nitrocellulose using Bio-Rad system (70V, 350 mA, 40 min)
3. Block the membrane for non-specific binding in Odessy Blocking buffer for 1 hr at RT.
4. Dilute the primary antibodies in Odyssey blocking buffer containing 0.1% Tween 20. (i.e. make a cocktail of the three antibodies (P*AKT, P*S6RP and P*RSK) by diluting each 1:1000). Incubate shaking overnight in cold room
5. Wash membrane 4×5 min at RT in PBS with 0.1% Tween 20.
6. Dilute the fluorescently-labeled secondary antibodies (1:10,000) in Odessey Blocking Buffer containing 0.1% Tween
7. Incubate blote in secondary antibody for 60-90 min at RT. Avoid prolonged exposure to light.
8. Wash membrane 4×5 min at RT in PBS with 0.1% Tween 20. Protect from light.
9. Rinse membrane in PBS to remove residual Tween-20. The membrane is now ready to scan.
Scan Membrane
1. Scan in the appropriate channels and protect the membrane from light until it has been scanned. The signal will be stable for several months, if protected from light. Membrane may be stores in PBS buffer at 4° C. or stored dry.
2. Quantify the bands using the Odessy software and normalize to loading control (mAb)

What is claimed is:

1. A compound of the Formula A:

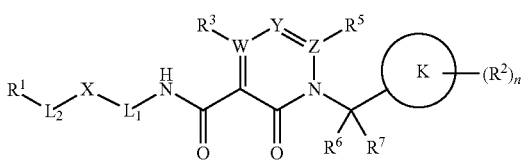

wherein:
n is 0, 1, 2, 3, 4 or 5;
W is C, Y is N, Z is C;
X is O, $CH_2$ or NH;
Ring K is aryl or heteroaryl;
$L_1$ is $C_0$-$C_6$ alkyl, $C_2$-$C_6$ alkenyl or heteroaryl, wherein said alkyl is optionally substituted with $C_1$-$C_6$ alkyl or phenyl, wherein said phenyl is optionally substituted with $C_1$-$C_6$ alkyl, $C_1$-$C_6$ alkyl-OH, O($C_1$-$C_6$)alkyl, halo and OH;
$L_2$ is $C_0$-$C_6$ alkyl, $C_2$-$C_6$ alkenyl or heteroaryl, wherein said alkyl is optionally substituted with $C_1$-$C_6$ alkyl or phenyl;
$R^1$ is heterocyclyl which is optionally substituted with $C_1$-$C_6$ alkyl, $C_1$-$C_6$ alkyl-OH, O($C_1$-$C_6$)alkyl, NH(C=O)$C_1$-$C_6$ alkyl, $C_2$-$C_6$ alkenyl, $CO_2H$, halo, OH, oxo and $NR^8R^9$;
$R^2$ is independently selected from: H, $C_1$-$C_6$ alkyl, $C_1$-$C_6$ alkyl-OH, O($C_1$-$C_6$)alkyl, $C_2$-$C_6$ alkenyl, $CO_2H$, halo, OH and $NR^8R^9$;
$R^3$ is selected from: H, $C_1$-$C_6$ alkyl, $C_1$-$C_6$ alkyl, O($C_1$-$C_6$) alkyl, $C_2$-$C_6$ alkenyl, $CO_2H$, halo, OH and $NR^8R^9$ when W is C;
$R^5$ is selected from: H, $C_1$-$C_6$ alkyl, $C_1$-$C_6$ alkyl-OH, O($C_1$-$C_6$)alkyl, $C_2$-$C_6$ alkenyl, $CO_2H$, halo, OH and $NR^8R^9$;
$R^6$ and $R^7$ are independently selected from: H and $C_1$-$C_6$ alkyl; and
$R^8$ and $R^9$ are independently selected from: H and $C_1$-$C_6$ alkyl;
or a pharmaceutically acceptable salt or a stereoisomer thereof.

2. The compound according to claim 1 of the Formula B:

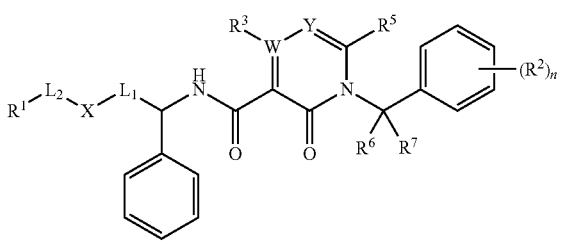

wherein:
n is 1, 2 or 3;
W is C and Y is N;
X is O, $CH_2$ or NH;
$L_2$ is $C_0$-$C_6$ alkyl, $C_2$-$C_6$ alkenyl or heteroaryl, wherein said alkyl is optionally substituted with $C_1$-$C_6$ alkyl or phenyl;
$R^1$ is heterocyclyl which is optionally substituted with $C_1$-$C_6$ alkyl, $C_1$-$C_6$ alkyl-OH, O($C_1$-$C_6$)alkyl, NH(C=O)$C_1$-$C_6$ alkyl, $C_2$-$C_6$ alkenyl, $CO_2H$, halo, OH, oxo and $NR^8R^9$;
$R^2$ is halo;
$R^3$ is selected from: H, $C_1$-$C_6$ alkyl, $C_1$-$C_6$ alkyl-OH, O($C_1$-$C_6$)alkyl, $C_2$-$C_6$ alkenyl, $CO_2H$, halo, OH and $NR^8R^9$ when W is C;
$R^5$ is selected from: H, $C_1$-$C_6$ alkyl, $C_1$-$C_6$ alkyl-OH, O($C_1$-$C_6$)alkyl, $C_2$-$C_6$ alkenyl, $CO_2H$, halo, OH and $NR^8R^9$;
$R^6$ and $R^7$ are independently selected from: H and $C_1$-$C_6$ alkyl; and
$R^8$ and $R^9$ are independently selected from: H and $C_1$-$C_6$ alkyl;
or a pharmaceutically acceptable salt or a stereoisomer thereof.

3. The compound according to claim 2 of the following formula:

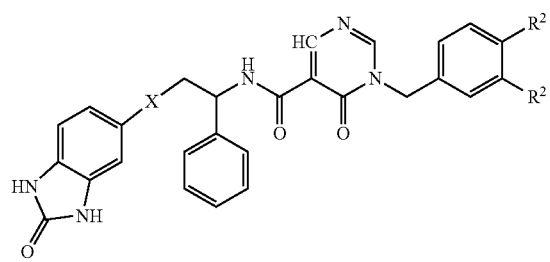

wherein:
X is O or NH; and
$R^2$ is halo;
or a pharmaceutically acceptable salt or a stereoisomer thereof.

4. A compound according to claim 1 which is:
1-(3,4-difluorobenzyl)-6-oxo-N-{(1R)-2-[(2-oxo-2,3-dihydro-1H-benzimidazol-5-yl)oxy]-1-phenylethyl}-1,6-dihydropyrimidine-5-carboxamide;
or a pharmaceutically acceptable salt or a stereoisomer thereof.

5. A pharmaceutical composition comprising a pharmaceutical carrier, and dispersed therein, a therapeutically effective amount of a compound of claim 1.

* * * * *

SEQUENCE LISTING

<160> NUMBER OF SEQ ID NOS: 1

<210> SEQ ID NO 1
<211> LENGTH: 28
<212> TYPE: PRT
<213> ORGANISM: Artificial Sequence
<220> FEATURE:
<223> OTHER INFORMATION: Completely Synthetic Amino Acid Sequence

<400> SEQUENCE: 1

Gly Gly Asp Gly Ala Thr Met Lys Thr Phe Cys Gly Gly Thr Pro Ser
 1               5                  10                  15

Asp Gly Asp Pro Asp Gly Gly Glu Phe Thr Glu Phe
            20                  25